(12) United States Patent
Ferraresi

(10) Patent No.: US 10,744,013 B2
(45) Date of Patent: Aug. 18, 2020

(54) TREATMENT DEVICE FOR ANEURYSMS PREFERABLY OF AORTIC KIND

(71) Applicant: KARDIA S.R.L., Milan (IT)

(72) Inventor: Roberto Ferraresi, Milan (IT)

(73) Assignee: KARDIA S.R.L., Milan (IT)

( * ) Notice: Subject to any disclaimer, the term of this patent is extended or adjusted under 35 U.S.C. 154(b) by 120 days.

(21) Appl. No.: 16/097,880

(22) PCT Filed: Feb. 21, 2017

(86) PCT No.: PCT/IB2017/050976
§ 371 (c)(1),
(2) Date: Oct. 31, 2018

(87) PCT Pub. No.: WO2017/191511
PCT Pub. Date: Nov. 9, 2017

(65) Prior Publication Data
US 2019/0133796 A1     May 9, 2019

(30) Foreign Application Priority Data
May 2, 2016   (IT) .............................. UA2016A3080

(51) Int. Cl.
*A61F 2/954* (2013.01)
*A61F 2/07* (2013.01)
*A61F 2/06* (2013.01)

(52) U.S. Cl.
CPC ............... *A61F 2/954* (2013.01); *A61F 2/07* (2013.01); *A61F 2002/061* (2013.01); *A61F 2210/009* (2013.01)

(58) Field of Classification Search
CPC .... A61F 2/06; A61F 2/07; A61F 2/856; A61F 2/954; A61F 2002/061; A61F 2210/009
See application file for complete search history.

(56) References Cited

U.S. PATENT DOCUMENTS 6,264,662 B1   7/2001 Lauterjung
2005/0020908 A1   1/2005 Birkenbach et al.
(Continued)

FOREIGN PATENT DOCUMENTS

DE         197 32 126 A1      3/1999

OTHER PUBLICATIONS

Cook Medical: "Zenith—Endovascular aortic repair—Fenestrated", 2014, XP002765066, retrieved from the Internet: URL: https://www.cookmedical.com/data/resources/AL-BUSM-FENTSP-EN-201402-M3.pdf [retrieved on Dec. 8, 2016].

*Primary Examiner* — George J Ulsh
(74) *Attorney, Agent, or Firm* — Vorys, Sater, Seymour and Pease LLP

(57) ABSTRACT

Provided is a treatment device for aneurysms. The device may include an endoprosthesis including a main channel and secondary openings and configured to be inserted in a main blood vessel (V1) at the point of an aneurysm and of a second blood vessel (V2), a first guide wire configured to be inserted in the endoprosthesis when inside the blood vessel (V1), through the main channel and a secondary opening, a second guide wire configured to be inserted inside the main blood vessel (V1) and the secondary blood vessel (V2), first magnetic means placed at the first guide wire, second magnetic means placed at the second guide wire, the magnetic means being mutually attracted and at least one of the magnetic means being mobile along its guide wire; means of moving the mobile magnetic means.

7 Claims, 4 Drawing Sheets

(56) References Cited

U.S. PATENT DOCUMENTS

2006/0161244 A1 7/2006 Seguin
2014/0277335 A1 9/2014 Greenberg et al.
2014/0364929 A1 12/2014 Ahari

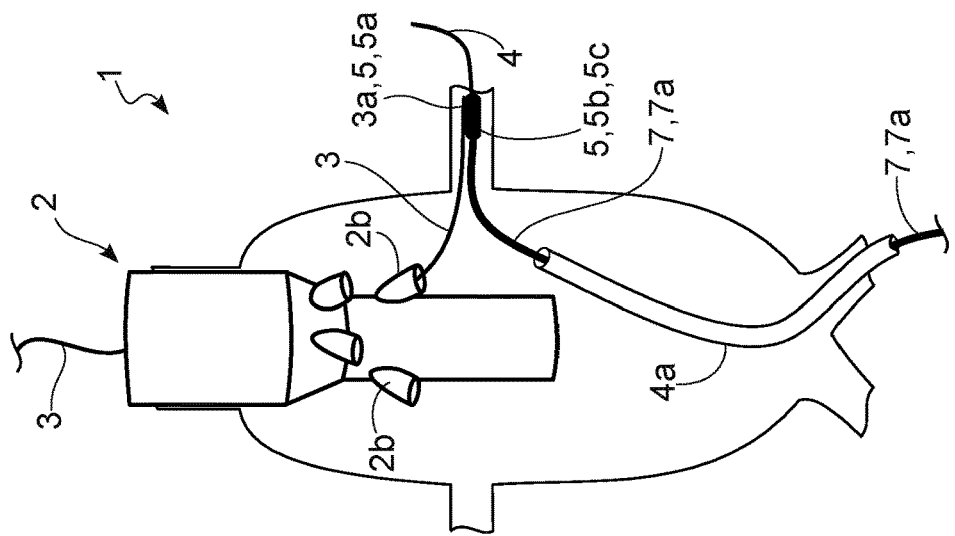
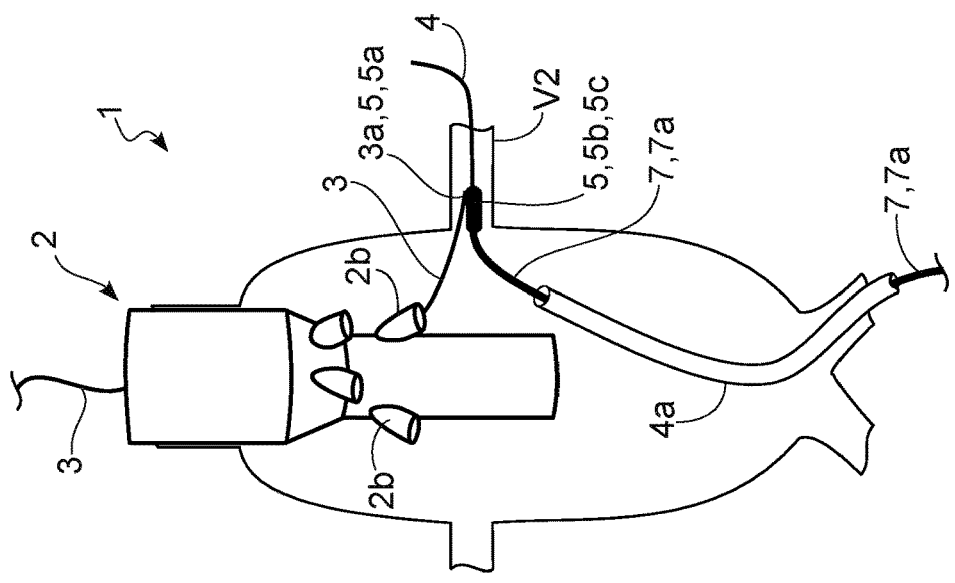
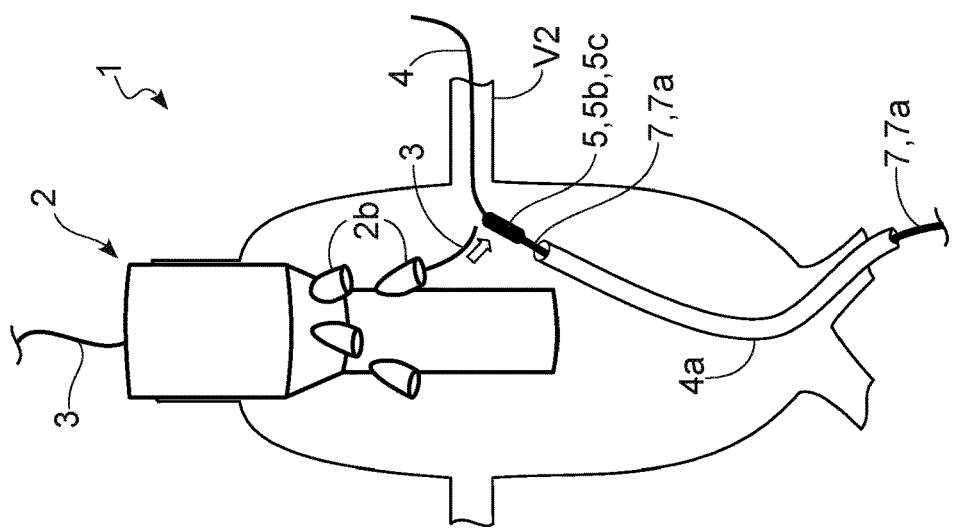

TREATMENT DEVICE FOR ANEURYSMS PREFERABLY OF AORTIC KIND

The present invention relates to an aneurysm treatment device preferably at the aorta of the type as recited in the preamble of the first claim.

As is known, aortic aneurysms are significant expansions of the aorta caused by the collapse of the walls of the aorta.

Said aneurysms are highly dangerous to the patient's life and, consequently, must be promptly treated.

Currently aortic aneurysms are treated using open surgery or via an endovascular approach using endoprostheses.

Endoprostheses are diametrically expandable tubular structures which can cover the aneurysm in its entirety and thereby reconstitute a proper channel for blood flow, excluding the aneurysmal sac from said blood flow.

To insert an endoprosthesis a guide wire is first inserted along the section of the aorta, for example on a radioscopic guide. The endoprosthesis is then pushed forward along the guide wire while in a diametrically contracted configuration.

The endoprosthesis is then expanded to re-establish a new channel for blood flow. In the case of extensive aneurysms of the thoracic or abdominal aorta, which affect the origin of important secondary arterial branches of the aorta itself, the endoprosthesis may cover the aorta and be provided with tubular extensions which are placed at said arterial branches also occupying the initial portion thereof, in order to allow the blood flow in these secondary arterial branches while continuing to exclude the aneurysmal sac.

For example, such branches may be the anonymous trunk, the carotids, the subclavian, the renal arteries, the celiac tripod, the mesenteric, iliac, lumbar or other branches.

In such cases the endoprosthesis must comprise openings and/or arms that extend, at least partially, into said arteries or branches.

For these operations so-called fenestrated endoprostheses are sometimes used.

Such endoprostheses comprise in fact, a plurality of ramifications and/or fenestrations for housing secondary endoprostheses which are inserted inside such arteries and which connect the body of the main endoprosthesis to such secondary arteries, allowing blood flow and continuing to exclude the aneurysmal sac from such flow.

For example, fenestrated endoprostheses are described in the document: Cook Medical: "Zenith—Endovascular aortic repair—Fenestrated", 2014, XP002765066, or even in the patent application US-A-2014/277335.

In such cases the surgeon passes a guide wire through the endoprosthesis, through a fenestration or an arm of said endoprosthesis and also through at least a portion of secondary artery, so as to be able to guide the secondary endoprosthesis and position it to bridge the body of the main endoprosthesis and secondary artery allowing the blood flow and excluding the aneurysmal sac.

Said fenestrated endoprostheses and the introduction of the secondary endoprostheses raise several problems.

First of all, in these areas, the aorta and the arteries that derive from it have a huge anatomical variability from one patient to another, creating the need for customized endoprostheses for each individual patient.

The production of said customised endoprostheses is performed following a three-dimensional vascular study of the patient and subsequent design of the prosthesis. Said procedures are very long and complex and a long time passes before their completion with consequent costs of tens of thousands of euros.

On account of such costs and times said procedures are not always feasible.

Secondly, even in the case of customised endoprostheses, the cannulation procedure of the secondary arteries and positioning of the secondary endoprostheses can be extremely complex and laborious as the operator is forced to work with catheters and guide wires that must necessarily pass through the fenestrations or branches of the main endoprosthesis and try to cannulate the secondary arteries inside the aneurysmal sac in anatomical conditions which are often unfavourable.

On account of said complexity the positioning of fenestrated endoprostheses is a lengthy procedure, requires prolonged radiological exposure of the patient and operators and use of large amounts of iodinated contrast medium.

Some systems with reciprocal magnetic attraction guide wires have tried to remedy such inconvenience when the operation occurs inside the thoracic aorta. Such as for example the methods and devices described in the patent applications: DE-A-19732126 and U.S. Pat. No. 6,264,662. However such methods and devices are not applicable to fenestrated endoprostheses.

In this situation the technical purpose of the present invention is to devise a treatment device for aneurysms able to substantially overcome the drawbacks mentioned above.

Within the sphere of said technical purpose one important aim of the invention is to provide a treatment device for aneurysms which is simple and economical.

Another important purpose of the invention is to provide a treatment device for aneurysms which can be adapted to many patients.

The technical purpose and specified aims are achieved by a treatment device for aneurysms as claimed in the appended Claim 1.

Preferred embodiment examples are described in the dependent claims.

The characteristics and advantages of the invention are clearly evident from the following detailed description of preferred embodiments thereof, with reference to the accompanying drawings, in which:

FIG. 3a is the device according to the invention in a first phase of utilisation;

FIG. 3b is the device according to the invention in a second phase of utilisation;

FIG. 3c is the device according to the invention in a third phase of utilisation;

FIG. 3d is the device according to the invention in a fourth phase of utilization;

FIG. 3e is the device according to the invention in a fifth phase of utilization;

Figure 2:
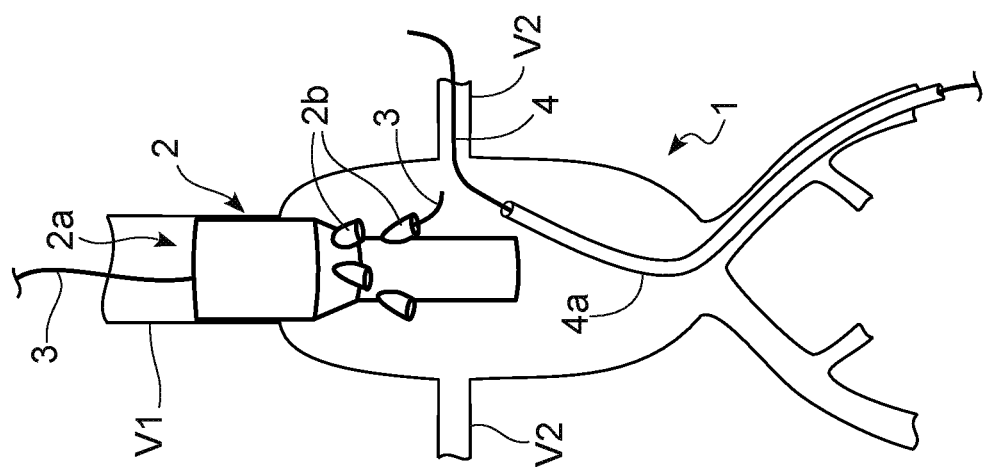
FIG. 2 shows, in cross-section, a second portion of the device according to the invention.
Figure 2:
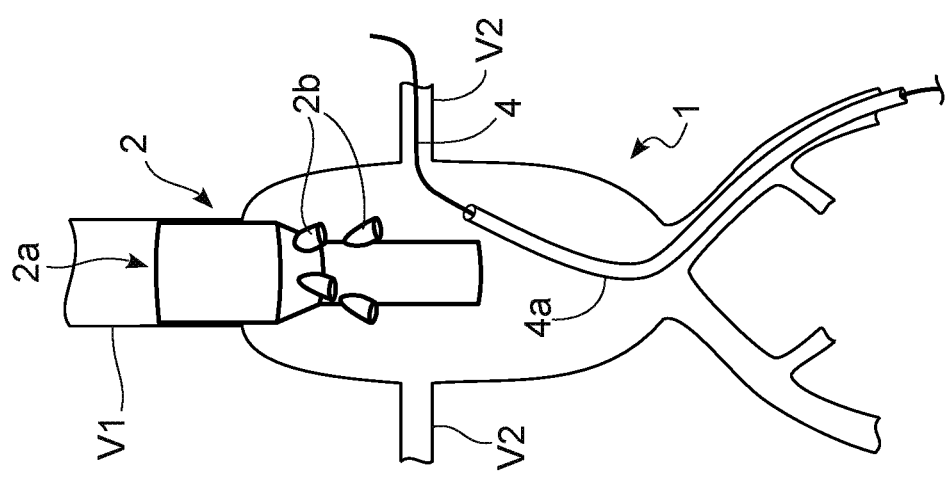
Figure 1:
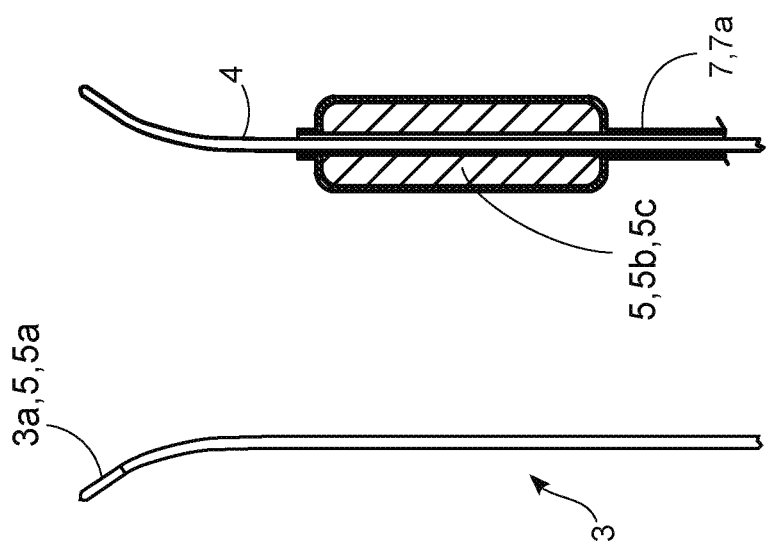
FIG. 1 shows a first portion of the device according to the invention.

Herein, the measures, values, shapes and geometric references (such as perpendicularity and parallelism), when used with words like "about" or other similar terms such as "approximately" or "substantially", are to be understood as except for measurement errors or inaccuracies due to production and/or manufacturing errors and, above all, except for a slight divergence from the value, measure, shape or geometric reference which it is associated with. For example, said terms, if associated with a value, preferably indicate a divergence of not more than 10% of said value.

In addition, where used, terms such as "first", "second", "upper", "lower", "main" and "secondary" do not necessarily refer to an order, a priority relationship or relative position, but may simply be used to more clearly distinguish different components from each other.

Except where specified otherwise, as evidenced by the discussions below, it should be noted that terms such as "processing", "computer", "computing", "evaluation" or the like, reference is made to the action and/or a processes of a computer, or similar electronic calculation device, which handles and/or processes data represented as physical, such as electronic magnitudes of logs of a computer system and/or memories, in other data similarly represented as physical quantities inside computer system, logs or other information storage, transmission or display devices.

With reference to the Drawings, reference numeral 1 globally denotes the device for treating aneurysms according to the invention.

It is suitable to treat aneurysms, particularly aortic aneurysms, for example of the abdominal aorta, namely aneurysms affecting the area connecting the thoracic-abdominal aorta and the arteries and/or its main branches.

The device 1 comprises an endoprosthesis 2, also improperly called stent, comprising a main channel 2a and secondary openings 2b and suitable to be inserted in a main blood vessel V1, preferably the aorta, at the point of an aneurysm and of a second blood vessel V2, for example a renal artery.

The endoprosthesis 2 is known per se, for example under the name of "fenestrated stent graft" or "multi-branched stent-graft".

The endoprosthesis 2 consists of a mainly tubular structure, possibly comprising ramifications for example for said arteries or in addition for the iliac arteries. Said tubular structure is expandable, so that the endoprosthesis may be inserted along the blood vessels while in the contracted configuration and can be subsequently expanded so as to cover the blood vessel in particular at the aneurysm. The main channel 2a of the endoprosthesis, after its insertion, substantially constitutes the wall of the blood vessel replacing the natural ectatic wall.

The secondary openings 2b may be simple holes along the wall of the main channel or may also comprise portions of secondary endoprostheses, known per se.

A similar endoprosthesis is for example produced by Cook Medical® under the trade name of Zenith® Fenestrated Endovascular Graft.

The device 1 further comprises a first guide wire 3 suitable to be inserted in the endoprosthesis 2 when inside the blood vessel V1, through the main channel 2a and a secondary opening 2b.

Said first guide wire 3 is, apart from the characteristics mentioned below, of the type known per se and is used for example for channelling the endoprosthesis when in the contracted configuration, or even for the removal of blockages in the blood vessels or for other operations performed in radioscopy. Similar guide wires are for example manufactured by Boston Scientific® under the trade name of Starter™ Guidewire.

The device 1 further comprises a second guide wire 4, suitable to be inserted into the main blood vessel V1 and the secondary blood vessel V2 not through the endoprosthesis and appropriately by a different route from the endoprosthesis. The guide wire 4 can also be inserted through a hollow tubular element 4a. The guide wire 4 can be inserted in the secondary arterial branch even before positioning the main endoprosthesis, so that the cannulation manoeuvre of said branch is easier to perform.

Said second guide wire 4 is, apart from the features described below, similar to the first guide wire 4 and of the same type.

The device 1 further comprises magnetic means 5. In particular first magnetic means 5a are placed at the first guide wire 3, and second magnetic means 5b are placed at the second guide wire 4, suitable to mutually attract each other.

They can be permanent magnets, electromagnets or ferromagnetic elements. Preferably, as hereinafter described, one of them is a permanent magnet. In addition, preferably the other of the magnetic means 5 is a ferromagnetic element.

In addition, at least one of the magnetic means 5, and preferably only one, is mobile along its guide wire 3, 4. Such magnetic means are hereinafter referred to as mobile magnetic means 5c.

Preferably, only one of the magnetic means 5 are mobile magnetic means 5c, while the others are fixed. Preferably the second magnetic means 5b are the mobile magnetic means 5c while the first magnetic means 5a are fixed.

More in detail the mobile magnetic means 5c comprise a permanent magnet and also preferably consist of a body comprising a through cavity suitable to allow the mobile magnetic means 5c to be slidingly constrained to its said guide wire 3 or 4, and preferably to the second guide wire 4, so as to slide along said guide wire 3 or 4.

The first magnetic means 5a consist of at least one head 3a of a guide wire 3 or 4, preferably of the first guide wire 3, made of ferro-magnetic material. Also a top portion, above the head, can be made of ferromagnetic material.

The device 1 further comprises movement means 7 of the mobile magnetic means 5.

The movement means 7 preferably comprise a cable 7a cable sliding along one of the guide wires 3 or 4 to move said mobile magnetic means 5c. Said cable is constrained to the body comprising the through cavity and preferably surrounds it externally.

The functioning of the treatment device 1 described above in functional terms is as follows and defines a new aneurysm treatment procedure.

In such procedure an endoprosthesis 2, of the type described, is inserted in the main blood vessel V1, in particular the aorta in an area affected by the aneurysm, in particular at a thoracic-abdominal aortic aneurysm and possibly with one or two expansions in the iliac arteries, using a procedure known per se. In particular a guide wire brings the endoprosthesis 2 in the contracted configuration to the aneurysm and subsequently the endoprosthesis 2 is expanded using known means.

The main channel 2a substantially constitutes the new blood vessel.

The secondary openings 2b are instead placed near the secondary vessels V2, for example renal arteries.

The second guide wire 4 is inserted through the secondary vessel V2, in particular the renal artery (FIG. 3a). The insertion of the second guide wire 4 may also be performed prior to the positioning of the main endoprosthesis.

The second guide wire 4 is inserted preferably in a retrograde manner, for example through the iliac artery and the aorta.

Since the second guide wire 4 is inserted before the main endoprosthesis or in any case outside the body of the endoprosthesis, cannulation of the secondary artery is smooth and easy to perform.

The first guide wire 3 is also inserted, not necessarily subsequently to the second guide wire 4, fitted with first magnetic means 5a preferably consisting of the ferromagnetic head 3a. Said first guide wire 3 is inserted through the aorta, the endoprosthesis 2, and then the main channel 2a, and a secondary opening 2b (FIG. 3b). Said guide wire 3 can be inserted from above and from below.

Subsequently, using the movement means 7, and in particular the cable 7a, the second magnetic means 5b are moved and in particular the hollow body consisting of a permanent magnet which is brought close to the connection between the main and secondary blood vessels V1 and V2 (FIG. 3c).

In such position the first and second magnetic means 5a and 5b are mutually attracted and preferably reciprocally magnetically connected in contact (FIG. 3d).

At this point the movement means 7 also move the first guide wire 3 along with the second magnetic means 5b. The first guide wire then enters, without difficulty, the secondary blood vessel V2 (FIG. 3e).

Figure 3G:
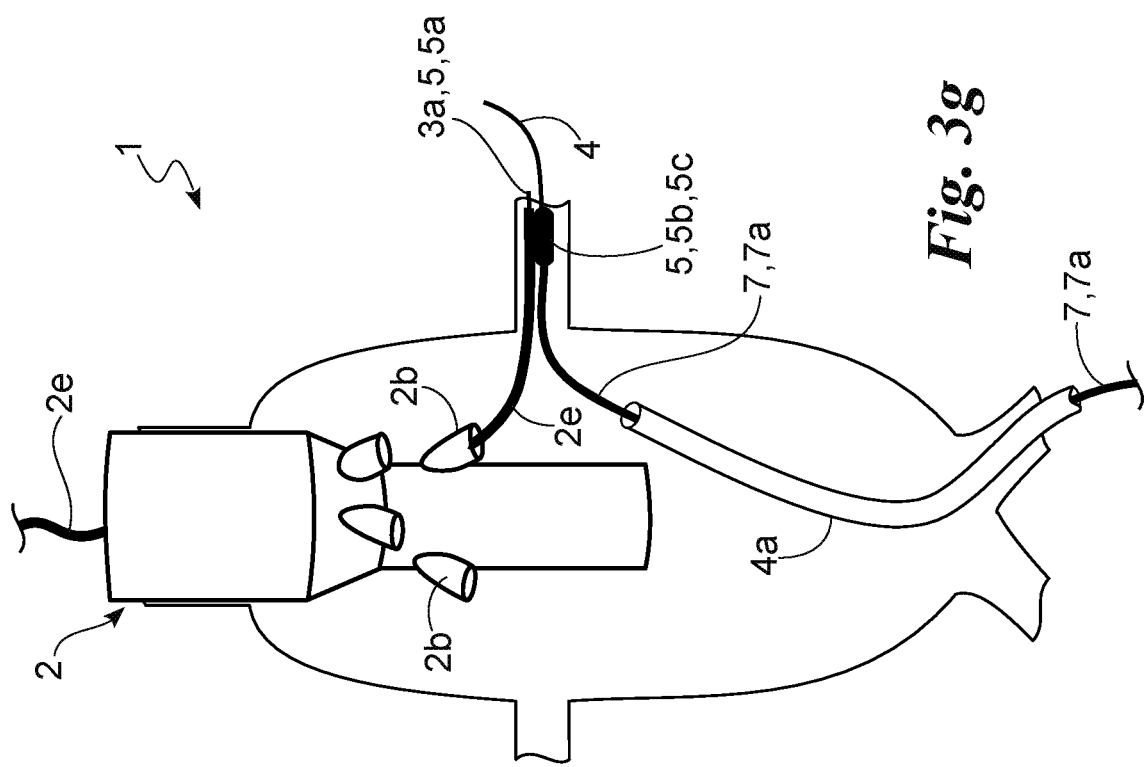
FIG. 3g is the device according to the invention in a seventh phase of utilization.
Figure 3F:
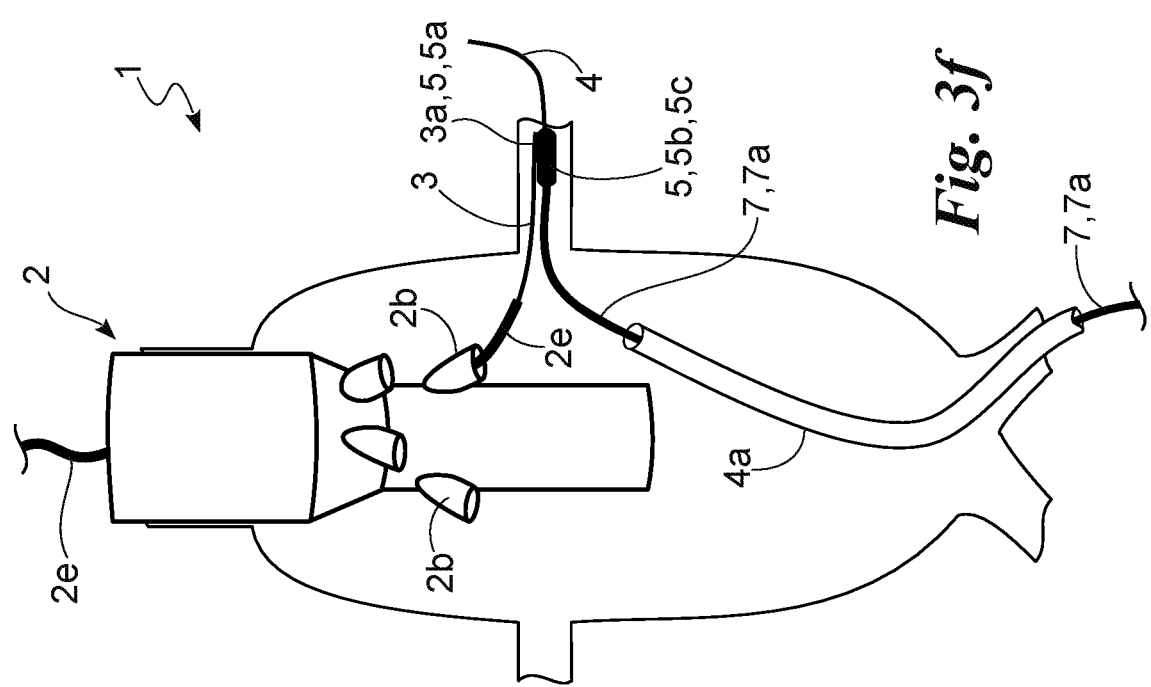
FIG. 3f is the device according to the invention in a sixth phase of utilization.

The magnetic means 5 can then be removed. Such removal may be performed by inserting an auxiliary channel 2e insertable in the first guide wire (FIG. 3F) and suitable to separate the magnetic means 5 so as to be able to mutually distance them (FIG. 3g).

When the auxiliary channel 2e, of appropriate rigidity, comes to the tip of the guide wire 3, it separates the magnetic head 3a from the second mobile magnetic means 5c, thereby allowing the removal of the second mobile magnetic means 5c without the guide wire 3 moving from the position reached.

The auxiliary channel can then be removed and the secondary blood vessel V2 remains free for the insertion of the secondary stent.

Figure 3L:
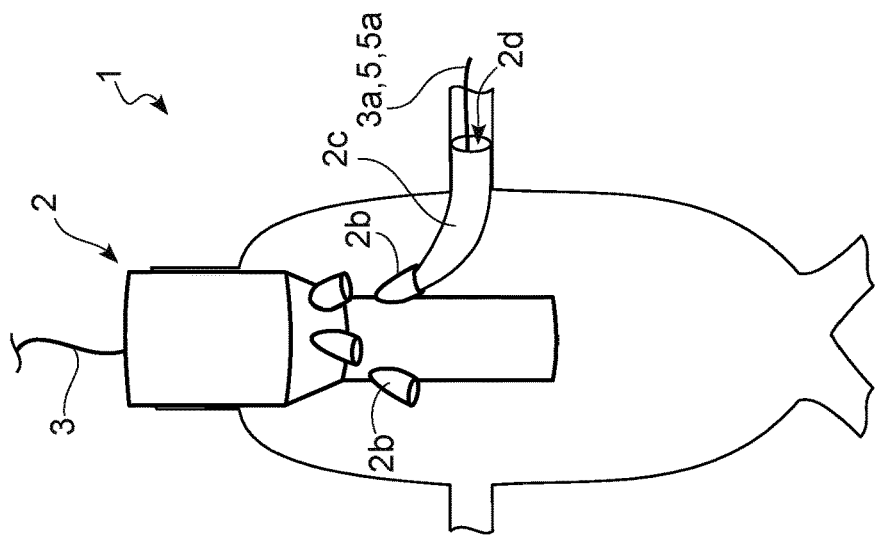
FIG. 3l is the device according to the invention in a tenth phase of utilization.
Figure 3I:
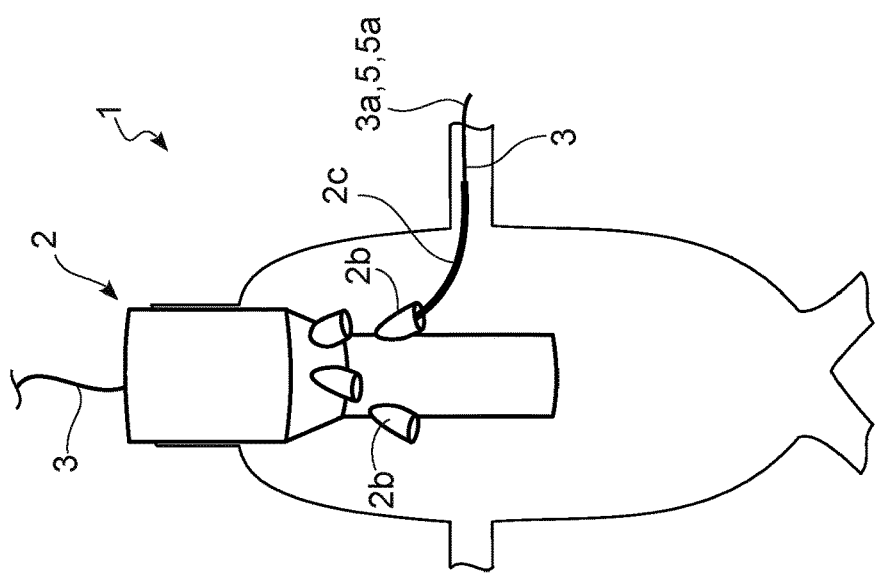
FIG. 3i is the device according to the invention in a ninth phase of utilization.
Figure 3H:
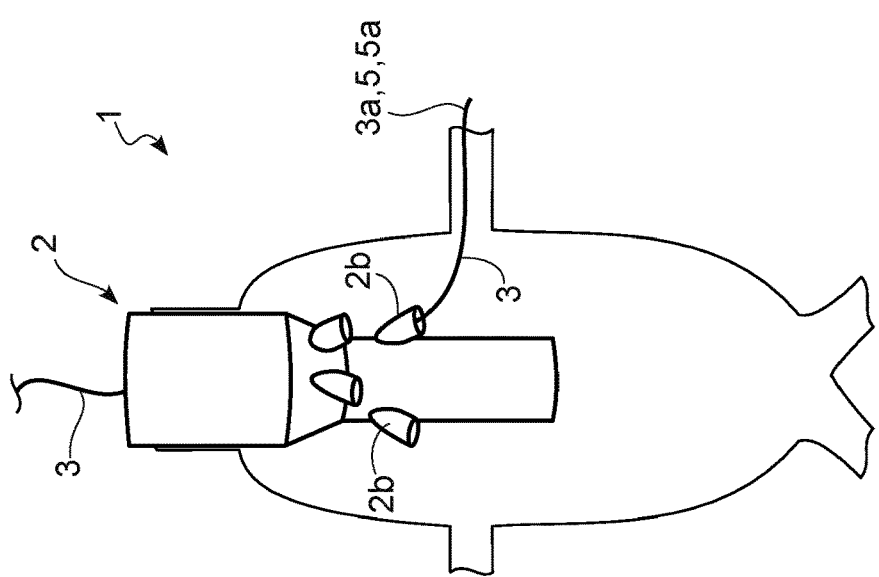
FIG. 3h is the device according to the invention in an eighth phase of utilization.

At this point (FIG. 3h) the secondary endoprosthesis 2c can be inserted through the guide consisting of the first guide wire 3, which passes through the secondary opening (FIG. 3i) and which constitutes a secondary channel 2d in fluidic through connection with the main channel 2a. The secondary endoprosthesis 2c is expanded and thus repairs the aneurysm in the secondary blood vessel V2 (FIG. 3l).

Such operation can be repeated for multiple secondary vessels V2.

The device 1 according to the invention achieves important advantages.

In fact, the insertion of a guide wire 4 through the aorta and artery in a retrograde fashion is much faster, the time required being as much as ten times lower.

The same method also allows the use of endoprostheses in which the secondary openings are not customised to the patient, given that the procedure and the device described overcome such problem and arrive in any case at the secondary vessels V2 through the same openings, even if not perfectly aligned.

The method thus makes it possible to use substantially standard fenestrated type prostheses immediately available in the haemodynamics laboratory with enormous advantages in terms of costs and production time.

Variations may be made to the invention without departing from the scope of the inventive concept defined in the claims. For example the guide wires 3 and 4 can be inserted on the same side or directly through the secondary V2 or other blood vessel. Moreover, both magnetic means may be mobile 5c.

In said sphere all the details may be replaced with equivalent elements and the materials, shapes and dimensions may be as desired.

The invention claimed is:

1. A treatment device for aneurysms, comprising:
   an endoprosthesis comprising a main channel and secondary openings configured to be inserted in a main blood vessel (V1) at the point of an aneurysm and of a second blood vessel (V2),
   a first guide wire configured to be inserted in said endoprosthesis when inside said main blood vessel (V1), through said main channel and one of said secondary openings,
   a second guide wire configured to be inserted inside said main blood vessel (V1) and said secondary blood vessel (V2),
   first magnetic means placed at said first guide wire,
   second magnetic means placed at said second guide wire, and
   said first magnetic means and said second magnetic means being mutually attracted,
   wherein at least one of said first magnetic means and said second magnetic means consists of mobile magnetic means along its said first guide wire or said second guide wire,
   wherein the device comprises movement means of said mobile magnetic means, and
   wherein said mobile magnetic means of a body comprising a through cavity configured to allow said mobile magnetic means to be constrained in sliding to its said guide wire so as to slide along its said guide wire.

2. The treatment device according to claim 1, wherein said mobile magnetic means comprise a permanent magnet.

3. The treatment device according to claim 2, wherein one of said magnetic means consists of at least a head of one of said guide wires made of ferro-magnetic material.

4. The treatment device according to claim 1, wherein said movement means comprise a cable sliding along one of said guide wires and configured to move said mobile magnetic means.

5. The treatment device according to claim 4, wherein said cable is constrained to said body comprising said through cavity.

6. The treatment device according to claim 1, wherein said second magnetic means are mobile along said second guide wire.

7. The treatment device according to claim 1, wherein one of said magnetic means consists of at least a head of one of said guide wires made of ferro-magnetic material.

* * * * *